United States Patent
Cormack et al.

(10) Patent No.: US 6,311,084 B1
(45) Date of Patent: Oct. 30, 2001

(54) RADIATION SEED IMPLANT METHOD AND APPARATUS

(76) Inventors: Robert A. Cormack, 465 Atherton St., Milton, MA (US) 02186; Anthony V. D'Amico, 13 Highland St., Weston, MA (US) 02493; Hanne M. Kooy, 8 Cannon St., Newton, MA (US) 02461; Clare M. Tempany, 59 Constellation Wharf, Charlestown, MA (US) 02129

( * ) Notice: Subject to any disclaimer, the term of this patent is extended or adjusted under 35 U.S.C. 154(b) by 0 days.

(21) Appl. No.: 09/304,996

(22) Filed: May 4, 1999

Related U.S. Application Data (60) Provisional application No. 60/084,165, filed on May 4, 1998.

(51) Int. Cl.[7] ............................. A61B 6/00; A61M 36/12
(52) U.S. Cl. ............................. 600/411; 600/7; 600/439; 600/427
(58) Field of Search .................................. 600/427, 439, 600/461, 1–3, 7, 411; 128/922

(56) References Cited

U.S. PATENT DOCUMENTS

| | | | |
|---|---|---|---|
| 5,205,289 | * | 4/1993 | Hardy et al. ...................... 128/653.1 |
| 5,227,969 | * | 7/1993 | Waggener et al. .............. 364/413.26 |
| 5,859,891 | * | 1/1999 | Hibbard ................................. 378/62 |
| 6,064,904 | * | 5/2000 | Yanof et al. .......................... 600/414 |
| 6,083,167 | * | 7/2000 | Fox et al. ............................. 600/439 |
| 6,095,975 | * | 8/2000 | Silvern ................................. 600/439 |
| 6,097,994 | * | 8/2000 | Navab et al. ......................... 700/245 |
| 6,129,670 | * | 10/2000 | Burdette et al. ..................... 600/427 |
| 6,139,544 | * | 10/2000 | Mikus et al. ........................... 606/21 |

OTHER PUBLICATIONS

Sullivan, K.J. et al., "Evaluating the Mediator Method: Prism as a Case Study," *IEEE transactions on Software Engineering* 22:8 (Aug. 1996).

Blasko, J.C. et al., "Transperineal Percutaneous Iodine—125 Implantation for Prostatic Carcinoma Using Transrectal Ultrasound and Template Guidance," *Endocure, Hypertherm, Oncol.* 3 pp. 131–139 (1987).

Nath, R. et al., "Dosimetry of interstitial brachytherapy sources: Recommendations of the AAPM Radiation Therapy Committee Task Group No. 43," *Med. Phys.* 22(2) pp. 209–234 (Feb. 1995).

Meli, J.A. et al., "Dose Distribution" in *Interstitial Brachytherapy —Physical, Biological and Clinical Considerations*, (NY:Raven Press) p. 21 (1990).

* cited by examiner

Primary Examiner—Marvin M. Lateef
Assistant Examiner—Shawna J Shaw
(74) Attorney, Agent, or Firm—Hamilton, Brook, Smith & Reynolds, P.C.

(57) ABSTRACT

A computer based method and apparatus for providing prostate brachytherapy using Interventional Magnetic Resonance imaging is described. The invention utilizes the excellent soft tissue visualization that Interventional Magnetic Resonance provides to produce radiographic, geometric and dosimetric feedback to an implant treatment planner (software module). The feedback enables an iterative procedure for the placement of needles based upon cumulative dosimetric feedback on the effect of the current and prior needle placements. The invention allows a treatment plan to be developed and the implantation procedure to be performed initially in accordance with the developed treatment plan. Modifications to the plan are made in real-time by the invention software module coupled to the IMR imaging system. The implantation procedure continues with the modified plan where further modifications are made to the plan with placement of each subsequent needle. Calculation of final coverage is also provided for ending evaluation of the implant procedure.

15 Claims, 9 Drawing Sheets

RADIATION SEED IMPLANT METHOD AND APPARATUS

RELATED APPLICATION

This application claims the benefit of Provisional Application No. 60/084,165 filed May 4, 1998, the entire teachings of which are incorporated herein by reference.

BACKGROUND OF THE INVENTION

Patients with prostate cancer currently have access to a treatment alternative called prostate brachytherapy. This treatment alternative is performed as an outpatient procedure, has limited side effects and minimal interruption to daily living. Prostate brachytherapy combines transrectal ultrasound with radioactive seed implantation. Tiny radioactive seeds are permanently implanted directly into the middle of the cancer within the prostate gland during the prostate brachytherapy. The procedure is usually completed within 60–90 minutes. The cure rate of prostate brachytherapy compares favorably to surgery and external beam radiation therapy. More importantly, the side effects of brachytherapy seem to be more acceptable in that there is a very low risk of developing incontinence, impotence and rectal damage.

Using transrectal ultrasound, the prostate implant team determines the exact size of the prostate gland, the extent of the cancer and the amount of radioactivity required. This information determines the number of seeds needed and where they should be placed.

Typically, the patient arrives at the hospital two hours before the scheduled time of the procedure. The anesthesiologist determines the best type of anesthesia for the patient; generally a spinal anesthetic is administered so that the patient will have no feeling from the waist down.

Figure 1:
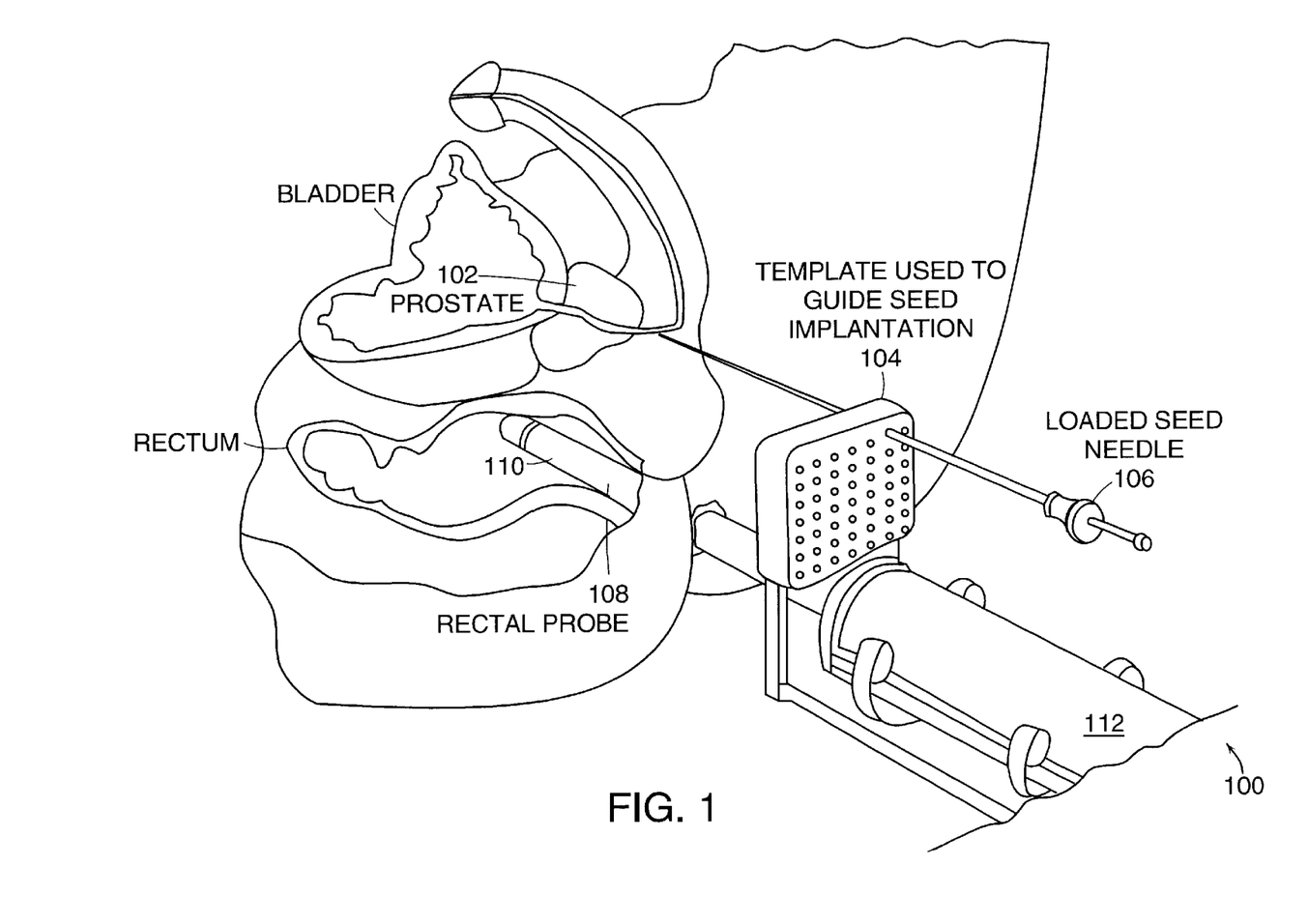
FIG. 1 is an illustration of the ultrasonic probe device with template guide used in the prior art.

After the anesthetic is administered, the prostate gland is located with transrectal ultrasound through a probe device shown in FIG. 1. The radioactive seeds are then placed within the prostate gland in a sequential fashion using needles inserted just behind the scrotum. Historically the needles are placed by hand, with template guidance. Ultrasound imaging, provides geometric feedback about the location of the needles, but does not provide the level of soft-tissue visualization of other imaging techniques. Dosimetric feedback is only available post-procedure, there is no option to adjust the implant dosage during the procedure based on dosimetric feedback. Thus, improvements in prostate brachytherapy are desired.

SUMMARY OF THE INVENTION

Prior art systems lack real-time dosimetric feedback and usually require post procedure dosimetry. Additionally, ultrasound imaging does not provide the excellent soft tissue visualization and 3-dimensional data acquisition of Interventional Magnetic Resonance imaging. Coupling the planning phase with the treatment phase in one session as in the present invention has the advantages of allowing the procedure to occur in a single day. This eliminates the prior art problem of re-aligning the patient to the exact position they were in for the planning phase when the treatment phase commences. Modification of the treatment plan is now possible during the procedure.

The present invention solves the disadvantages of the prior art and provides a radiation seed implant planning system. In another aspect, the present invention provides an improvement over the methods and devices used in prior art prostate brachytherapy. In particular, the present invention includes an imaging system device, a plurality of needles for expelling radioactive seeds, a needle template and a treatment planning and procedure module. The needle template contains working holes for the needles, calibration points for template registration and a guide hole for an orientation device. The treatment planning and procedure module includes: (i) a template registration process that uses the calibration points to map needle template coordinates into imaging system coordinates, (ii) a target definition module for selecting target and sensitive areas based upon images generated by the imaging system, and (iii) an implant planning module for creating a treatment plan incorporating real-time dosimetry.

The present invention provides image guided brachytherapy to target tissue areas by imaging (in real-time) the target tissue using an imaging system. A needle template is placed in proximity to the target tissue and the needle template location is mapped to the coordinate system of the imaging system. A user of the invention then defines the bounds of the tissue targeted for treatment on the planning system. The planner, using the planning system, creates a treatment plan for insertion of needles. According to the created treatment plan, each needle holds a predetermined number and spacing of radiation seeds and is inserted through working holes in the needle template. The seeds are placed and effect (dose) of the seeds is calculated. Radiographic, geometric and dosimetric feedback is acquired on the placement of the needle and the treatment plan may be modified based upon the acquired feedback. If the needle placement is acceptable a plurality of radioactive seeds are placed in the tissue from the needle. The procedure continues until all necessary needles are placed, and final coverage of treatment is evaluated using real-time images from the imaging system.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

FIG. 1 shows a typical ultrasound probe device 100 for carrying out the prior art radioactive seed implant procedure. A rectal probe 108 has a distal end 110 that serves as the working end and a proximal end 112 held by a physician. A template guide 104 is coupled to the rectal probe 108 and provides a plurality of holes/apertures for holding and guiding needles 106 substantially along axes parallel to the axis of the rectal probe 108. In particular, the different template holes guide the needles to different positions/locations entering the prostate gland 102. The rectal probe 108 provides ultrasound images of the needle 106 with respect to the prostate gland 102. These ultrasound images serve as feedback of needle location for the physician to determine if a different template hole should be used to more appropriately locate the needle in the prostate gland 102.

Figure 2:
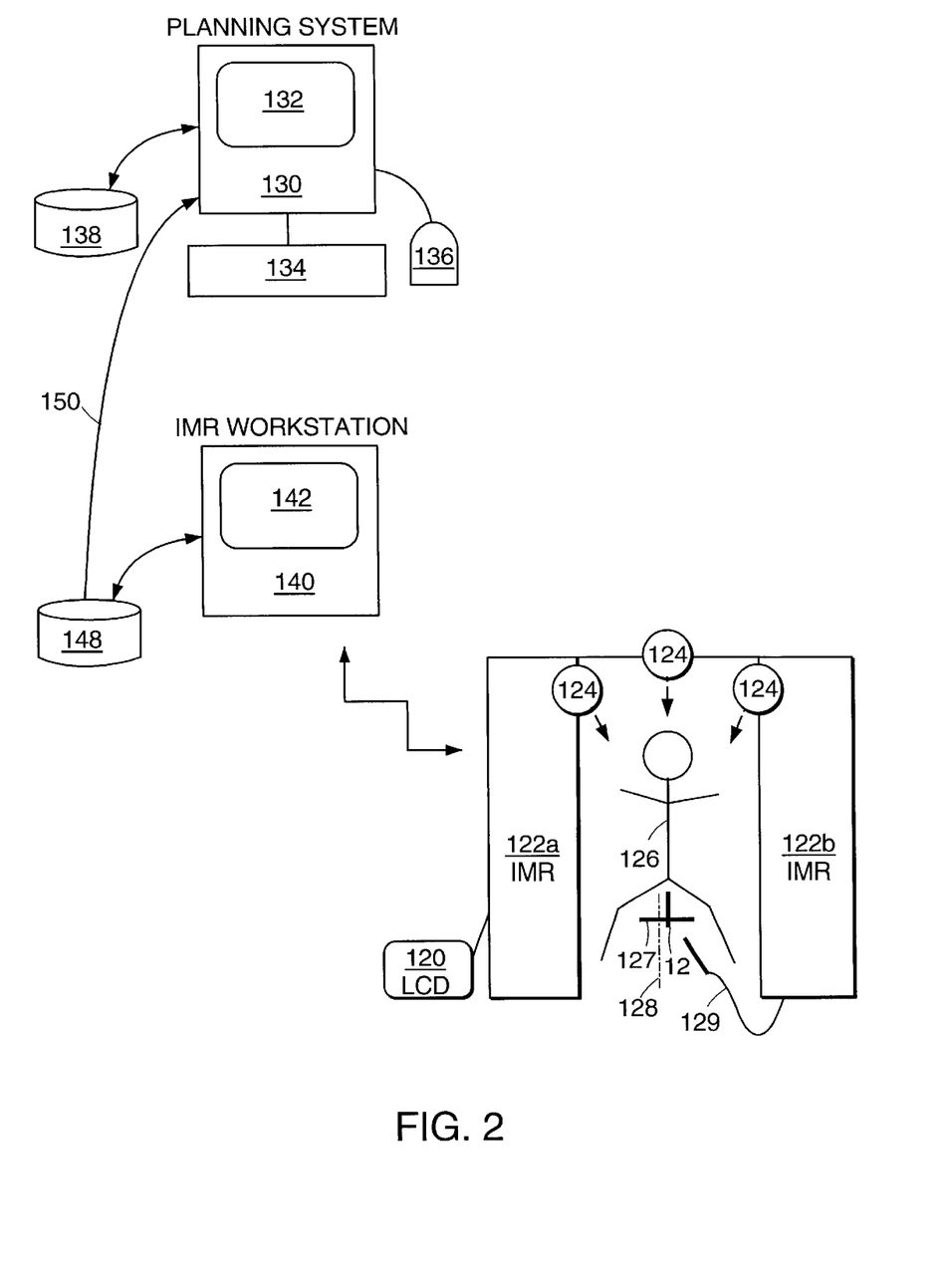
FIG. 2 is a schematic diagram of the radiation and planning system of the present invention.

By way of overview, FIG. 2 illustrates a radiation seed implant and planning system embodying the present invention. A patient 126 may either be placed in the imaging volume in the traditional manner, along the bore of the magnets (122a, 122b), or may be brought into the gap between the magnets (122a, 122b) on a couch that latches to the Interventional Magnetic Resonance ("IMR") unit from the side. The side-docked position is used because it allows placement of the patient in the lithotomy position with the lower legs supported by surgical boots mounted to the inner surfaces of the two rings of the IMR unit (122a, 122b). This arrangement allows access to both the patient's 126 perineum, for implantation, from one side of the magnet (122a, 122b) and to the patient's 126 head, for anesthesia, from the other side of the magnet (122a, 122b).

The IMR unit (122a, 122b) provides two methods of image acquisition. It may be operated in traditional mode acquiring a series of axial, sagital or coronal images, or it may also be operated in real-time mode, allowing rapid imaging of any plane within the imaging volume with a refresh time of approximately five seconds per image. The IMR unit is operated from an IMR workstation 140, which provides a screen 142 to display the images. The IMR workstation 140 also stores images on its own hard disk storage system 148. The IMR workstation is typically located outside the operating room. A display 120 is provided local to the IMR unit (122a, 122b) enabling physicians within the operating room to view the images.

With the patient 126 in place, the needle template 127 and an associated rectal obturator 12 mounting system (similar to rectal probe 108 in FIG.1) are positioned. Once the desired depth of the rectal obturator 12 is achieved, either by clinical judgement of the physician or with real time imaging guidance, it is locked into place relative to the needle template 127 by a set screw. The needle template 127 is then locked to the couch rails of the IMR unit, providing a fixed location for the needle template 127. The rectal obturator 12, which runs parallel to the expected paths of the needles fills the rectum and helps keep the rectum out of the trajectory of the needles 128. The rectal obturator 12 also provides a path of egress for air, preventing its build up within the rectum, which could lead to air pockets that would distort the patient's 126 anatomy. The template and mounting system provide prostate fixation, needle guidance and a base plane for the needle template 127 with respect to IMR coordinate system mapping. A series of light emitting diode ("LED") receivers 124 are used in conjunction with an LED transmitting wand 129 to determine geometry in the imaging system's coordinates.

The invention treatment and planning system 130 provides image acquisition, needle template calibration, volumetric contouring, dose calculation and feedback on the status of the implant procedure. The planning system 130 allows a planner to plan manipulations of the needles 128 and immediately see the dosimetric implications of the change. The planning system 130 includes a display 132 for displaying radiographic, geometric and dosimetric feedback about the current status of the treatment plan. A keyboard input device 134 and mouse 136 are used to input status into the planning system 130, including the specification of the tissue volumes of interest (target and sensitive structures) for treatment. Other input and output devices are also suitable.

A full set of volumetric scans, both so-called T1 and T2 weighted, is taken for target definition. The T1 series is most useful for the definition of the prostatic capsule, while the T2 series is used to differentiate the substructure of the prostate and determine the target structures for the procedure. The T2 axial series of 3 millimeter skip 0 is typically used to determine the target volume, with the T1 series providing a cross check.

Local storage is provided by way of a hard disk storage system 138 for storing images and information associated with the treatment plan. The planning system 130 is connected, by way of a shared file system connection 150 with the IMR workstation's hard disk storage system 148. This arrangement allows the planning system 130 to import IMR images for use in treatment planning and evaluation.

Figure 3:
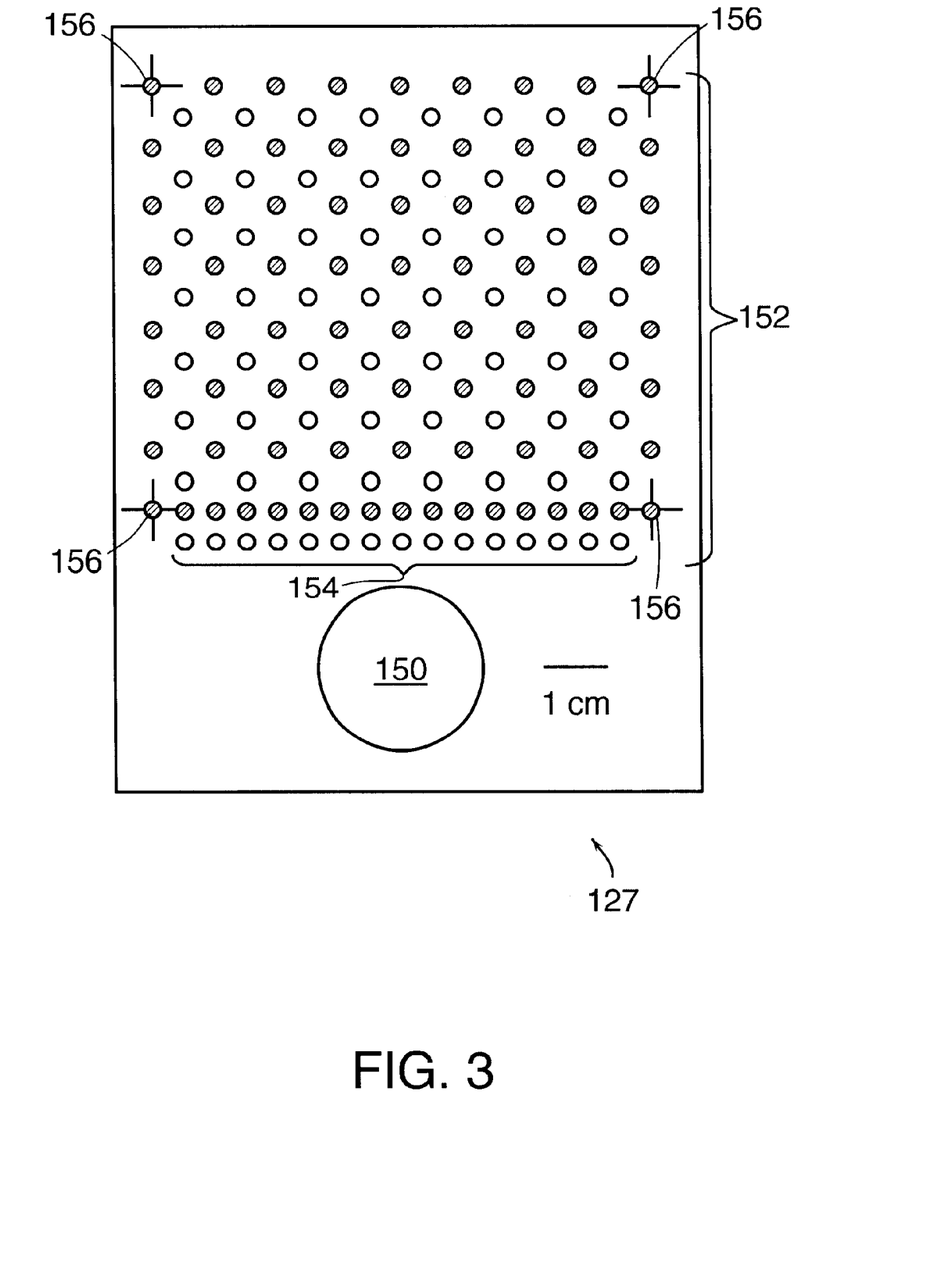
FIG. 3 is a schematic diagram of a needle template of the radiation seed implant planning system of the present invention.

FIG. 3 shows, by way of example, a needle template 127 with a 2 centimeter diameter rectal obturator guide hole 150 to accommodate a rectal obturator 12. The rectal obturator 12 assists in localizing the prostate. The needle template 127 has an array of working holes 152 for needle guidance. The working holes 152 are intended to accept an 18 gauge needle and guide it along a path perpendicular to the face of the needle template 127. The working holes 152 are drilled along two one centimeter grids offset by 0.71 centimeters both diagonally. Additional working holes 154 are located just anterior to the rectal obturator guide hole 150 to assist in achieving implant coverage to the posterior region of the prostate. Four of the working holes 152, are used as calibration holes 156 and are located in each of the four corners of the needle template 127. In the preferred embodiment, needle template 127 is an 8×10×2 cm piece of plastic.

Figure 4:
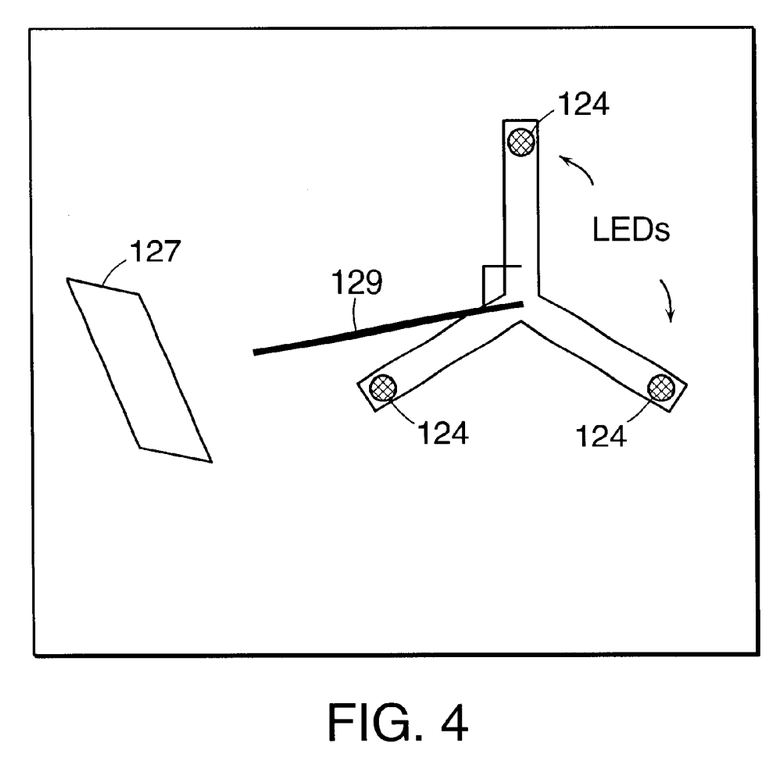
FIG. 4 is an illustration of the calibration sub-system for mapping the needle template coordinates to imaging system coordinates of the present invention.

FIG. 4 shows a calibration subsystem for determining the position of a plane in space relative to the coordinates of the imaging system (122a, 122b). Output from the calibration subsystem are used to map the needle template 127 coordinates to imaging system (122a, 122b) coordinates using a series of LED receivers 124 and a wand 129 with a LED transmitter. The transmitter is mounted on a point of known geometry on the wand 129 and the LED receivers 124 are mounted on the IMR unit (122a, 122b). The LED transmitter on the wand 129 is flashed at a known time and observed by the LED receivers 124 to allow the construction of the location point in three-dimensional space of the LED transmitter. Triangulation or other such techniques are employed for location construction calculation. In particular, the LED transmitter end of wand 129 is positioned and operated in each of the calibration holes 156 of the needle template 127, one hole 156 at a time. Location in 3D space of each of the calibration holes 156 and effectively of the plane of the needle template 127 results. From the calculated position of the LED transmitter points, the distance to the plane of the needle template 127 is determined using the prior mounting of the needle template 127. With the location and orientation of the needle template 127 determined, an image plane may be specified as an offset from the tip of the wand 129. This mapping is necessary for both the planning and implantation phases to be able to calculate the projection of a needle through a working hole 152 and onto any image plane acquired by the IMR unit (122*a*, 122*b*).

In the preferred embodiment, the wand 129 is attached to a one centimeter needle and inserted into a series of four calibration holes 156 on the template 127. The calibration subsystem is used to read out the three-dimensional imaging system coordinates of each of the holes. Three three-dimensional points are sufficient to determine the offset and rotation of the needle template 127 relative the to IMR unit (122*a*, 122*b*). The fourth calculated/determined point location is used to measure error in the calculated mapping from needle template 127 coordinates to imaging system coordinates. An example a calibration subsystem is the PIXSYS optical tracking system manufactured by Image Guided Technologies, Inc., Boulder, Colo.

Figure 5:
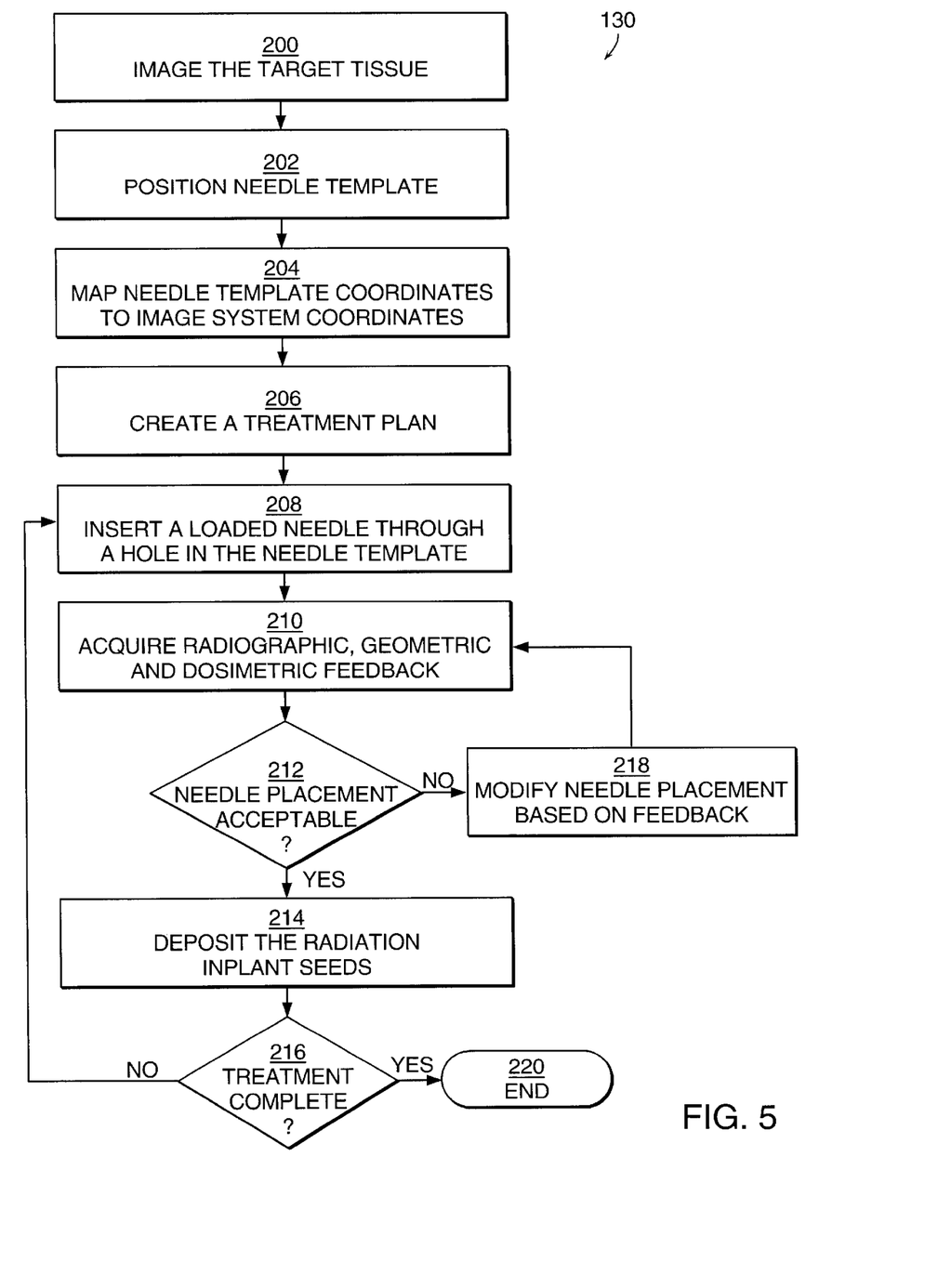
FIG. 5 is a flow diagram of the radiation seed implant and planning system of the present invention.

FIG. 5 is a flow diagram of the radiation seed implant and planning system 130 of the present invention. In step 200 an image is made of the target tissue using the IMR (122*a*, 122*b*) imaging system, the volumes of interest are specified on the planning system display 132 based upon the images transferred from the IMR workstation's hard disk 148. For each axial image in the T2 series of images the prostate peripheral zone, anterior rectal wall and urethra are specified by identifying pixels on the image using a cursor control device such as the mouse 136, as the image is viewed on the planning system display 132. The geometric information contained in each image file is used to calculate the 3D IMR imaging system coordinates of all identified/tagged pixels and map them onto voxels of a virtual cube containing the scanning volume of the IMR. The result is a 3-dimensional collection of tagged voxels representing the structures of interest, namely the prostate, anterior rectal wall and urethra. Once the voxels have been tagged, they may be projected onto any IMR image acquired with the same patient geometry allowing a cross check of the contoured anatomy with the T1 series, or with the later real-time images used during the implant procedure. This ability provides assurances that the anatomy has been properly identified, and that there has been no movement of the anatomy over the course of the implant.

In step 202 the needle template 127 is positioned and locked into place proximal to the patient 126 as described in the discussion of FIG. 2. In step 204 the needle template coordinate system is mapped to the imaging system coordinated as described in the discussion of FIG. 4.

A treatment plan is created in step 206 using the planning system 130. Planning the implantation of radiation seeds occurs in the needle template 127 coordinate system. The needle template provides an array of working holes 152, of known location which are used to guide the needles 128 into the patient. As the needle template 127 is fixed in imaging, system coordinates, and does not move during the procedure, its surface is the plane of reference from which to specify the depth of each needle 128 insertion. The approach common in prior art systems of specifying needle depths is to specify the depth in terms of centimeters relative to the base image. With the mapping from needle template 127 coordinates to imaging system coordinates complete, the projection of the needle template's working holes 152 onto an IMR image is calculated and overlaid on that image. The needle template working holes 152 are overlaid on the images used for volume identification to choose working holes 152 with projections that pass through the prostate while avoiding sensitive structures (e.g., rectum, urethra or bladder). The planning system 130 enables needle placements to be modeled; these modeled or "virtual needles" are manipulated as to depth and radiation seed loading, by the planner. Using a transperineal approach, and with the needle template roughly perpendicular to the sup-inf axis of the patient, a needle will enter the patient and progress more superior the deeper it is placed.

Each needle has two control variables, namely depth and loading. The depth of needle insertion is limited only by needle length Needles typically range from approximately 10 centimeters to approximately 20 centimeters in length depending on patient setup. A needle may contain a variable number of radioactive seeds, activity is selected from an inventory of available seed strengths. Seeds are placed starting at the tip of the needle and working to the needle base with a one centimeter distance measured from the center of each seed. The first seed will be placed deepest, and most superior within the patient.

The treatment plan is developed by manipulating one "virtual needle" at a time with the assistance of various types of feedback, including information about a needle's environment (radiographic and geometric feedback), summary graphs and overlays about dose distributions (dosimetric feedback). The "virtual needle" is a hypothetical graphics insertion into the images (previously) generated by the IMR. This graphics insertion is first defined in terms of the needle template coordinate system (i.e., which working hole, what depth or distance from the hole into the patient), then is mapped to the IMR image coordinate system for providing the radiographic and geometric feedback. Based on the hypothetical needle location in the image and the needle loading (number and spacing of seeds) specified by the physician in an appropriate screen view of the treatment plan portion of the invention software, the software module calculates dose distribution. This provides the dosimetric feedback. All feedback is updated in real-time as the planner interactively adjusts the treatment plan.

In particular, the software provides the planner/physician with radiographic and geometric feedback by way of a graph of the volume of target and sensitive tissues in a cylinder along the trajectory of the "virtual needle". This feedback assists in avoiding sensitive structures. The radiographic and geometric feedback suggests a depth of needle insertion, and a number of possible radiation seeds. The computer generated and displayed graph also shows the distribution of radioactivity along the needle to assure that the seeds are within the prostate gland.

In the preferred embodiment, the planning system uses an object oriented architecture with a strict parent-child hierarchy to ensure proper geometric relationships, and mediator based inter-object communications to ensure the propagation of information throughout the system. The transformation and communication functionality is built into a base object ("BaseObject") from which all objects in the system are derived.

The BaseObject implements operations, or methods, that permit file storage for treatment planning data, geometric transformations between instances, instance and class management, and mediator-based communications. The system has a notion of an absolute coordinate system defined by the needle template 127. The position of a seed is specified relative to a needle 128, and the needle 128 position is specified relative to the needle template. Thus, the position of a seed in the imaging coordinate system is determined by applying a geometric transformation, where each link in the object hierarchy has a geometric transformation defined for it.

Implementation of the objects associated with the physical process of implanting illustrate the parent-child hierarchy that maintains the geometric relationships between seed, needle and template 127. The needle template 127 defines the master coordinate frame and as such is the trunk of the parent-child tree. Based on the output of the calibration system (FIG. 4), the planning system 130 calibrates the imaging system to its reference frame, and as a result all future images are children of the needle template 127, and any point in the image may be transformed to needle template coordinates by way of the transformation defined between the needle template 127 and imaging system. The needle template 127 is the parent of all the working holes 152 for needle insertion. The working holes 152 know their location and orientation relative to the needle template 127. A needle 128 in turn is the child of a working hole 152 and knows its depth of insertion relative to the working hole 152, and a seed knows where it is with respect to the tip of its parent needle 128. To find the location of an object in the template reference frame, a composite coordinate transformation is calculated from the individual child to parent transformations. For example, adjusting the depth of insertion of a catheter only affects the transformation between needle 128 and its parent working hole 152, but will be automatically taken into account when the template coordinate of all the needles' child seeds are calculated.

Event propagation is handled by the mediator controlled inter-object communication. At class instantiation, each class declares all its possible events, and all events of other classes that would affect it. An event mediator then informs all other classes that have declared an interest in the event.

Figure 7:
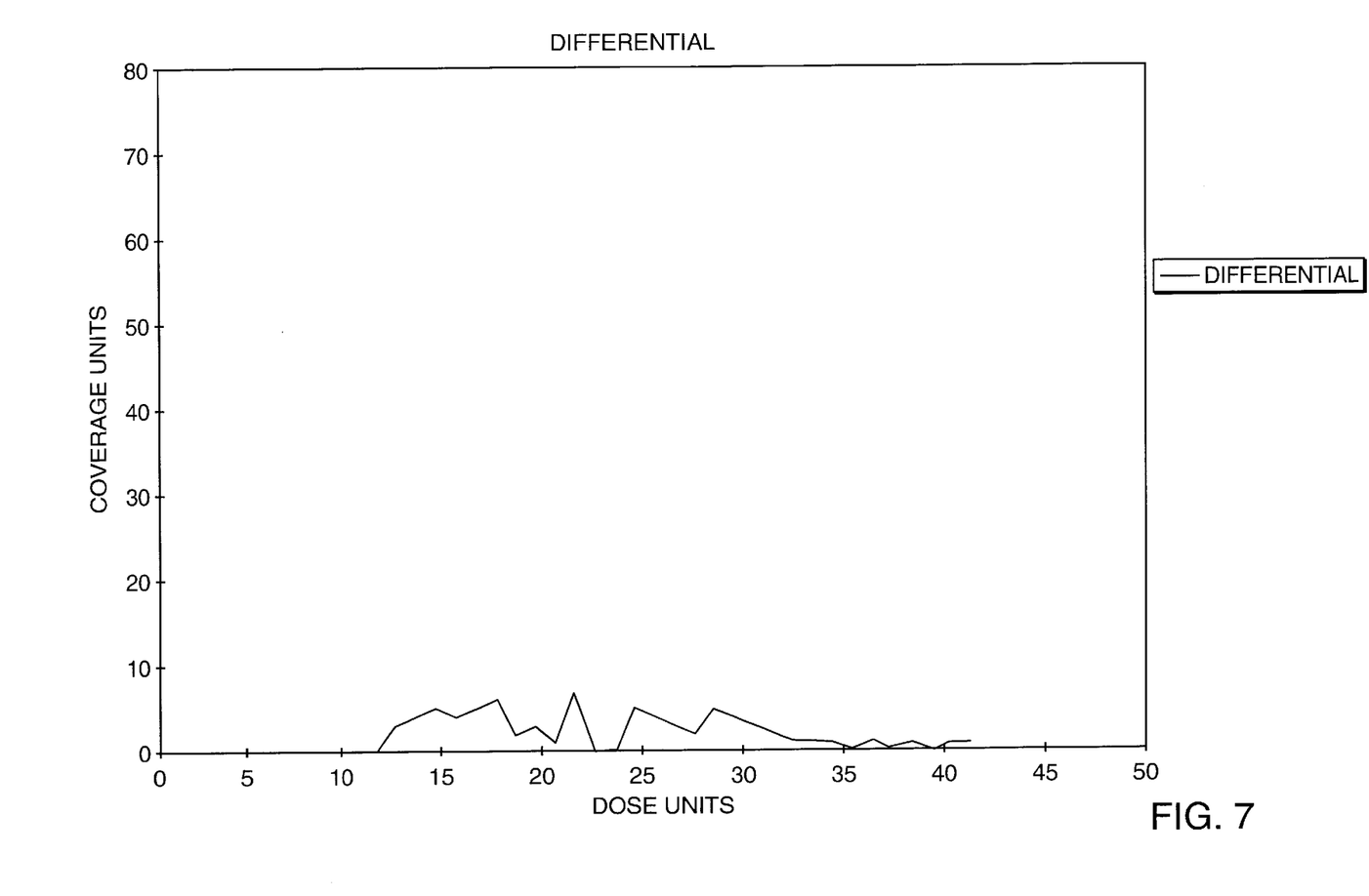
FIG. 7 is a schematic diagram of a differential dosage volume histogram of the present invention.
Figure 8:
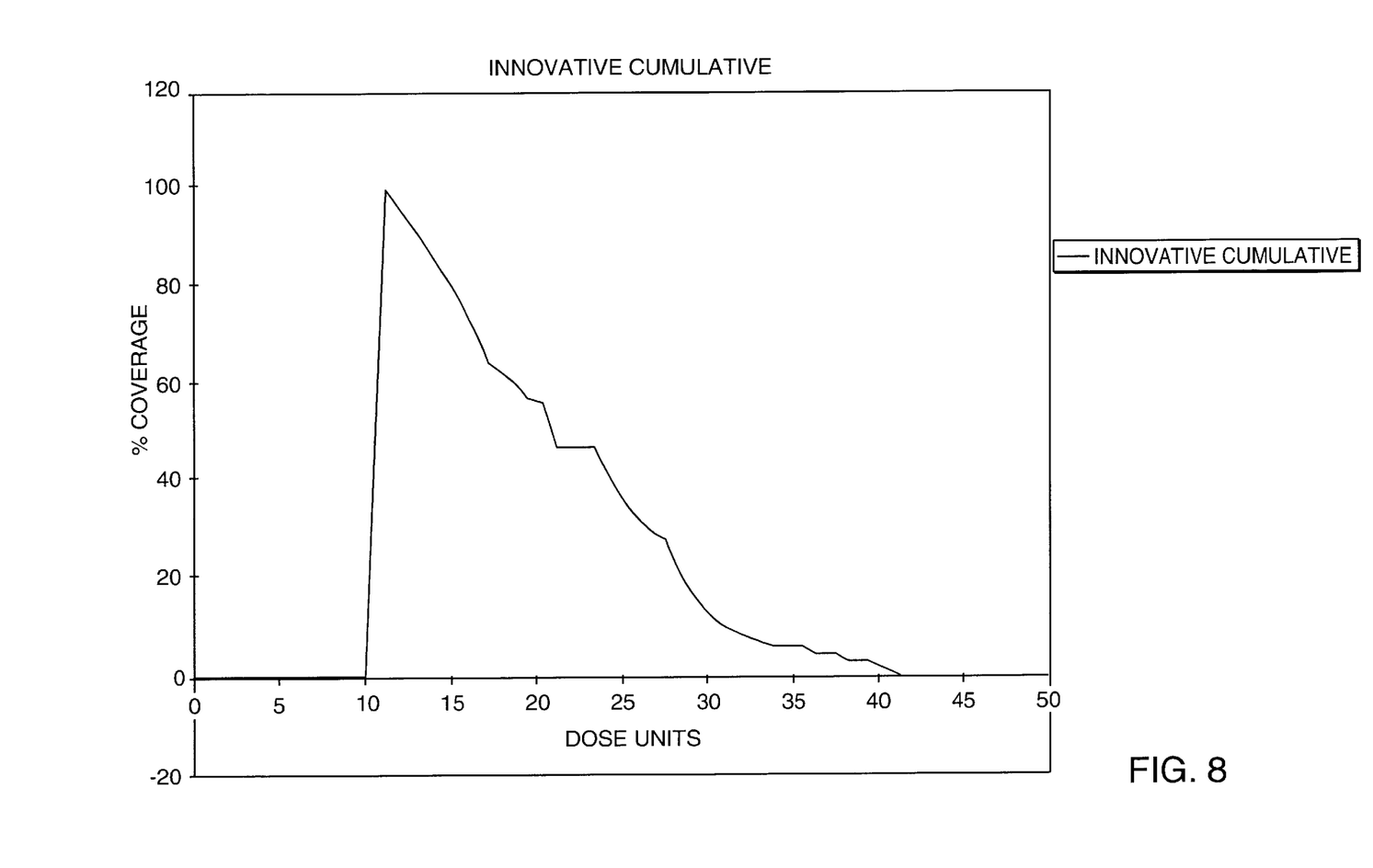
FIG. 8 is a schematic diagram of a innovative cumulative dosage volume histogram of the present invention.

Preferably, the invention software also provides the planner/physician with dosimetric feedback from a dose calculation engine using an algorithm based upon the recommendations of the AAPM Task Group 43 combining a geometric factor, a radial geometry correction, and an angular anisotropy correction. The software module calculates and in graphical form summarizes dose to all tagged or of-interest structures, in dose-volume histograms ("DVH") and percentage coverage plots ("PCP"), discussed later. The DVHs are presented in either traditional cumulative (FIG. 6) or differential form (FIG. 7). The cumulative DVH is also presented in an innovative format (FIG. 8). The PCP (FIG. 9) is a stacked bar graph that shows the percentage of target structure dosage coverage. Sample code for calculating DVH's and bar graphs is given in Appendix I.

Additionally, to assist in finding regions of the implant that need additional study, either due to poor dose coverage or excessive dose, isodoses may be overlaid on any image acquired from the IMR unit (122a, 122b). The dose calculations may either be displayed as actual dose distributions, or organ specific threshold displays indicating regions of dose below a structure's prescription dose or doses over a structure's tolerance dose. Each organ has individually specified minimum and maximum acceptable doses.

In the preferred embodiment, prostate prescription dose is 137 Gy, rectal tolerance is 87 Gy and urethral tolerance is 171 Gy.

Target structures have their prescription dose defined as a minimum dose, and 150% of prescription dose defined as a maximum dose. Sensitive structures have a minimum does defined as 0 and a maximum dose defined as their tissue tolerance dose. This organ specific display highlights only those regions that are below minimum acceptable dose (preferably displayed as blue) or over maximum acceptable dose (preferably displayed as red), while leaving all regions that are between minimum and maximum dose uncolored. Thus, a perfect plan would show no blue, and the only visible red would be within the target structure. This organ specific threshold display is useful to indicate where needles should be added, and suggesting regions where needles may be removed.

With these tools, the treatment planning system 130/step 206 (FIG. 5) enables the physician to come up with a configuration of needles 128, with associated depths and loadings, that will produce the desired dose distribution. A printout of the treatment plan is generated that includes a text printout of the needle template working holes 152 to be used, the depth to which each needle should be inserted, the radiation seed loading pattern, and a needle template's eye view of the needle distribution. A copy of the treatment plan is given to radiation safety personnel to load radioactive seed sources in the needles.

Using the plan created in step 206, a physician inserts a needle 128 through a specified working hole 152 in the needle template 127 under real-time imaging system guidance. Step 208 of the software (treatment planning system 130) is responsive. Each needle 127 has its depth marked along its shaft and is inserted while the imaging system acquires images in the coronal view. These coronal view images provide feedback to the physician as to whether the needle 128 is bending off its intended path.

The treatment plan is implemented by positioning one needle 128 at a time with the assistance of three types of feedback: radiographic, geometric and dosimetric acquired at step 210. Once the needle 128 is in location, sagital and axial images obtained by the imaging system 122a, 122b (FIG. 2) are read by the treatment planning system 130. The images are used to check that the needle 128 is within the prostate and not puncturing the rectum, urethra or bladder. Geometric feedback is provided by displaying the expected prior defined (hypothetical) needle location together with the observed needle location. If a clinically significant difference in location is observed the physician can reposition the needle 128 and start the feedback loop again. Once the needle 128 is in a desirable anatomical position the planning system is updated by clicking the mouse 136 on the image of the actual observed pixel location of the needle 128. Using the observed needle position and information contained in the header data stored with the image an observation point in three-dimensional imaging system coordinates is calculated. That point is used to calculate the actual needle 128 path in the patient and thus the location of the proposed radiation seed implants. The needle is assumed to follow a straight line, passing through the working hole 152 in the needle template 127 through which the needle 128 was inserted and the observed point on the image. The tip of the needle 128 is calculated to be the point along the line whose distance from the template is equal to the needle's 128 insertion depth. Once a needle 128 position is updated all geometric locations, dose calculations and summary statistics are updated. The dose calculation incorporates the observed location of all needles already placed and assumes ideal (prior defined hypothetical) placement of all remaining needles.

In step 212 the needle 128 placement is checked, if the placement is dosimetrically acceptable the physician deposits the radiation implant seeds in step 214.

In step 216 the overall status of the treatment is compared to the clinical goal of the treatment plan. If dosage coverage is acceptable the procedure is ended at step 220, if not the procedure continues at step 208. A dose distribution is considered acceptable even if the peripheral zone was not fully covered if: 1) the apex of the prostate gland does not contain any under-dosed regions, 2) there are no consistent under-dosed regions in the region of the anterior base consisting of more then 10% of the contoured volume, and 3) each under-dosed point is receiving at least 90% of prescription dose.

Figure 6:
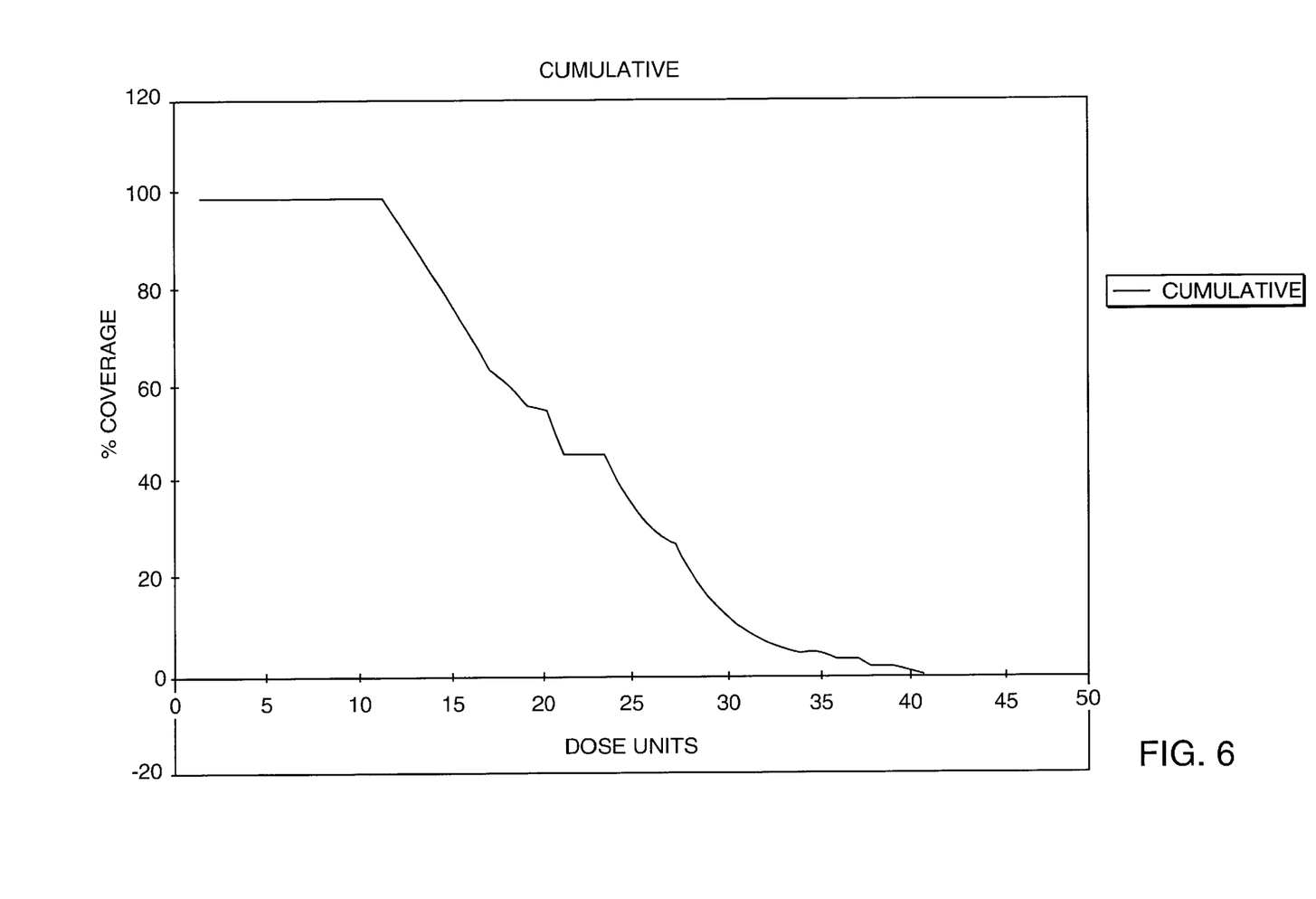
FIG. 6 is a schematic diagram of a cumulative dosage volume histogram of the present invention.

FIG. 6 is a schematic diagram of a cumulative dosage volume histogram of the present invention. A DVH is presented in either traditional cumulative or differential form. In traditional cumulative form, a horizontal line at 100% volume coverage is drawn from zero dose units through the minimum covering dose units (in the illustrated example 10 units) and then a curve down to zero volume coverage at 40+ dose units. The x-axis represents dose units and the y-axis represents percentage of coverage. For example, FIG. 6 shows a dose of thirty units occurring in approximately ten percent of tissue or structure of interest (tagged).

FIG. 7 is a schematic diagram of a differential dosage volume histogram of the present invention. A DVH is presented in differential form showing dose units relative to coverage units (e.g., cubic-centimeters). The x-axis represents dose units and the y-axis represents coverage units. For example, FIG. 7 shows a dose of fifteen units occurring in approximately four units (cc) of tissue or structure of interest (tagged).

FIG. 8 is a schematic diagram of a innovative cumulative dosage volume histogram of the present invention. A vertical line, from zero volume coverage to one hundred percent volume coverage is drawn at the minimum dose unit of 10. This representation gives better feedback about minimum dose levels to the target/tagged structure. For example, FIG. 8 shows a minimum dosage of ten units occurring in one hundred percent of structure of interest.

Figure 9:
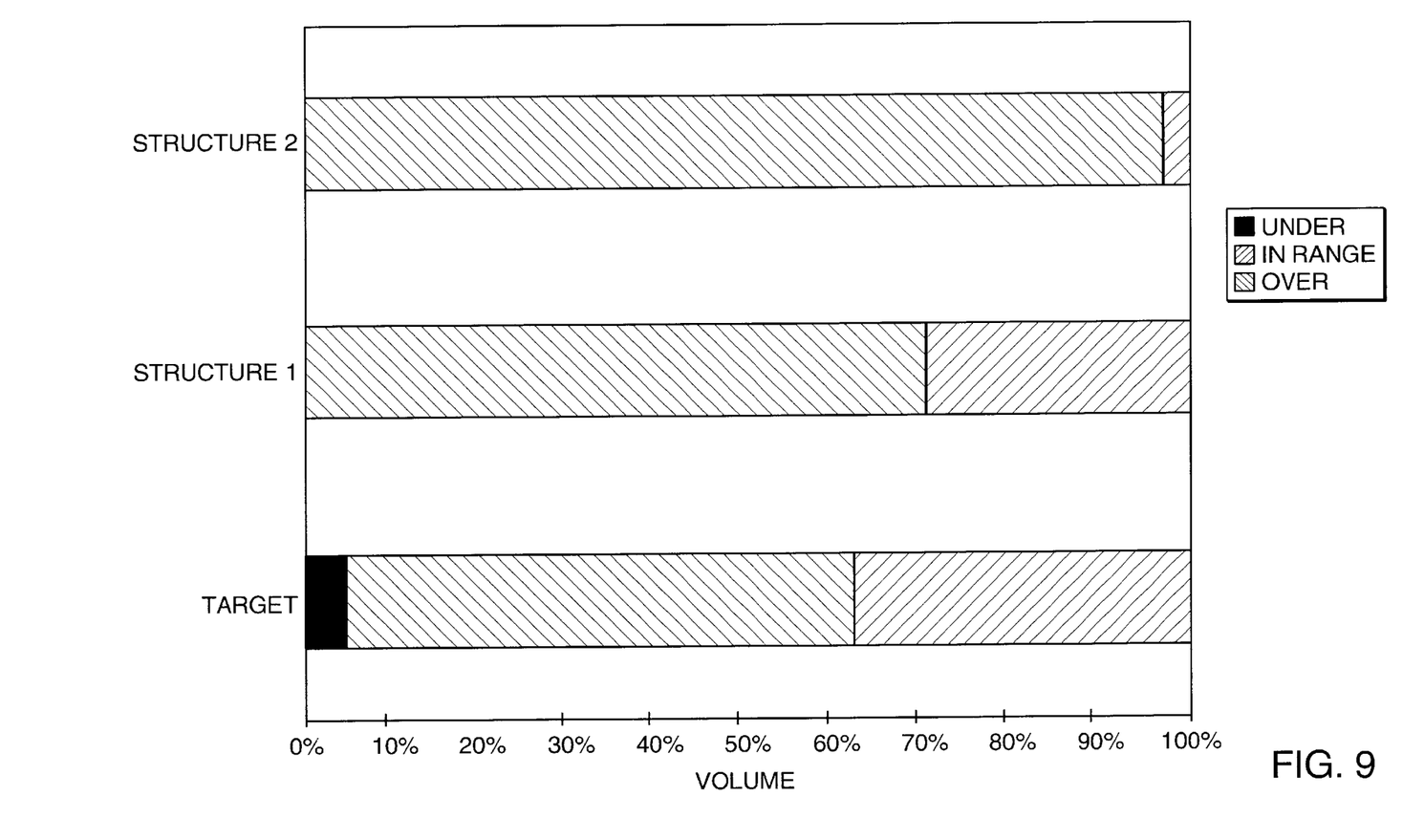
FIG. 9 is a schematic diagram of a percentage coverage plot of the present invention.

FIG. 9 is a schematic diagram of a percentage coverage plot of the present invention. The PCP is a stacked bar graph that shows the percentage of target/tagged structure areas that are: 1) under prescription dose, 2) between prescription dose and 150% of prescription dose, and 3) over 150% of prescription dose. Additionally, the PCP shows the percentage of sensitive structures that are: 1) under tolerance dose, and 2) over tolerance dose. The PCP format provides a simple summary plot providing easy determination as to whether a modification of a "virtual needle" increases or decreases dose coverage or sparing.

While this invention has been particularly shown and described with references to preferred embodiments thereof, it will be understood by those skilled in the art that various changes in form and details may be made therein without departing from the spirit and scope of the invention as defined by the appended claims.

For example, although radiation seeds are discussed as the implanted object, other heat-oriented elements or heat sources may be used. In response, the present invention system tracks relative geometry (positioning) of the heat sources and the cumulative (dosimetric) effect on the surroundings.

In another example, it is understood that although Interventional Magnetic Resonance imaging is discussed, various other imaging systems may be employed.

In a further example, although prostate brachytherapy is described, the present invention may be used for planning and treatment of other organs and tissues within the body.

Other input and output methods, including mouse pointing devices, joy sticks, stylus pointers, wands, touch screens and voice-activated pointers are appropriate for use with this invention.

APPENDIX I

```
*RAC99
this routine calculates the DVH(differential and cumulative) and
bar graphs for a chosen volume v.
The volume v has dps->npts points that have been defined as a
    part of that volume.
The dvh is a histogram of__DVH__NBIN__ bins
The loser bound of the graph is min__dose
The upper bound of the graph is max__dose
The bin size of therefore (max__dose - min__dose)/DVH__NBIN
*RAC99
void Dvh::calc__data__set(Volume *v){
int i;
double invdbin;
int index;
int vtag;
float val0[__DVH__NBIN__];
float val1[__DVH__NBIN__];
float val0p[__DVH__NBIN__];
float val1p[__DVH__NBIN__];
float val0d[__DVH__NBIN__];
float val1d[__DVH__NBIN__];
float dv;
float vtot,invdtot__percent;
float dcum0,dcum1;
dosePoints *dps;
float low0,mid0,high0;
float low1,mid1,high1;
int imin__thresh;
int imax__thresh;
dps =v->get__dosePoints( ); // get the pointer to the volume dose points
invdbin =__DVH__NBIN__/(max__dose - min__dose);
vtag =v->get__tag( );
if (vtag <=0) return;
*RAC99 initialize the arrays to accumulate the histograms *RAC99
for (i = 0; i <__DVH__NBIN__;i++){
    val0[i] = 0.;
    val1[i] = 0.;
    val0p[i] = 0.;
    val1p[i] = 0.;
    val0d[i] = 0.;
    val1d[i] = 0.;
}
vtot = 0.;
*RAC99
We loop over all the points in the volume.
Based on the dose at a point, the bin that corresponds to that dose
is incremented.
Doses that are out of range of the graph are binned into the first
or last bin
*RAC99
for (i = 0; i < dps->npts; i++) // accumulate histogram
    {
    dv = dps->dv[i];
    vtot+=dv; // keep track of total dose
// bin the dose points from total implant
    index = (dps->dose[i]-min__dose)*invdbin;
    index = (index < 0) ? 0: index;
    index = (__DVH__NBIN__ <= index) ? (__DVH__NBIN__-1) : index;
    val0[index] += dv;
    // bin the dose points from proposed implant
    index = (dps->dose__done[i]-min__dose)*invdbin;
    index = (index < 0) ? 0: index;
    index = (__DVH__NBIN__ <= index) ? (__DVH__NBIN__-1) : index;
    val1[index] += dv;
}
dcum0=0.;
dcum1=0.;
*RAC99
Here we calculate the cumulative DVH from the differential data just
accumulated.
*RAC99
if(vtot!=0.){
    invdtot__percent = 100./vtot; for (i = 0; i <__DVH__NBIN__;
    i++) {//scale for percent
and dvh
    val0p[i] = invdtot__percent * val0[i];
```

APPENDIX I-continued

```
    val1p[i] = invdtot_percent * val1[i];
    val0d[i] = 100. - dcum0;
    val1d[i] = 100. - dcum1;
*RAC99
Here we zero out the graph until we have the first dose at which the
volume is not 100% covered. This forces the vertical line that indicates
the minimum dose to the structure
*RAC99
    if (0. == dcum0)
        val0d[i] = 0.0;
    if(0. == dcum1)
        val1d[i]= 0.0;
        dcum0 += val0p[i];
        dcum1 += val1p[i];
        }
}
*RAC99 this is GUI interface *RAC99
XrtDataSetYData(data[_ALL_S_DVH_].percent_hist ,
        vol_to_dvh[vtag], val0p, DVH_NBIN_,0);
XrtDataSetYData(data[ALL_S_DVH_].percent_dvh
        vol_to_dvh[vtag], val0d,_DVH_NBIN_,0);
XrtDataSetYData(data[_OLD_S_DVH_].percent_hist,
        vol_to_dvh[vtag], val1p, _DVH_NBIN_,0);
XrtDatasetYData(data[_OLD_S_DVH_].percent_dvh
        vol_to_dvh[vtag], val1d, _DVH_NBIN_,0);
// imin_thresh = (min_bar[vol_to_dvh[vtag]] -min_dose)*invdbin;
// imax_thresh = (max_bar[vol_to_dvh[vtag]] - min_dose)*invdbin;
imin_thresh = (v->get_thrsMin( ) - min_dose)*invdbin;
imax_thresh = (v->get_thrsMax( ) - min_dose)*invdbin;
low0 = 0.; mid0 = 0.; high0 = 0.;
low1 = 0.; mid1 = 0.; high1 = 0.;
*RAC99
Here we loop over the accumulated differential histogram and count
how many points have dose (d) that is:
a: d<min_thresh
b: min_thresh < d <max_thresh
c: max_thresh < d
the fraction of points that are in each category a,b,c are used to
make up the bar graphs
*RAC99
for (i=0;i<_DVH_NDIN_;i++){
if( i < imin_thresh){
    low0 += val0p[i];
    low1 += val1p[i];
}
else if( imax_thresh < i)
    {
        high0 += val0p[i];
        high1 += val1p[i];}
else {
    mid0 += val0p[i];
    mid1 += val1p[i];}
}
*RAC99 this is GUI interface *RAC99
XrtDataSetYElement(data[_ALL_S_DVH].
bars,0,vol_to_dvh[vtag], low0);
XrtDataSetYElement(data[_ALL_S_DVH].
bars,1,vol_to_dvh[vtag], mid0);
XrtDataSetYElement(data[_ALL_S_DVH].
bars,2,vol_to_dvh[vtag], high0);
XrtDataSetYElement(data[_OLD_S_DVH].
bars,0,vol_to_dvh[vtag], low1);
XrtDataSetYElement(data[_OLD_S_DVH].
bars,1,vol_to_dvh[vtag], mid1);
XrtDataSetYElement(data[_OLD_S_DVH].
bars,2,vol_to_dvh[vtag], high1);
}
```

What is claimed is:

1. An image-guided method for implanting radiation seeds into target tissue comprising the steps of:
   (a) imaging the target tissue using an imaging system, the imaging system having a image coordinate system;
   (b) using images of the target tissue from the imaging system, creating a treatment plan for the target tissue;
   (c) in accordance with the created treatment plan, loading a needle with radiation seeds and placing the needle with respect to the target tissue to initiate implantation; during implantation:
   (d) acquiring radiographic, geometric and dosimetric feedback on the placement of the needle with respect to the target tissue;
   (e) modifying the created treatment plan based upon the acquired radiographic, geometric and dosimetric feedback, said modifying producing a modified treatment plan; and
   (f) placing the radiation seeds from the needle into the target tissue at a position relative to the needle and acceptable according to the modified treatment plan.

2. The method of claim 1 further comprising the steps of:
   (g) evaluating total effect of placed radiation seeds; and
   (h) for each subsequent needle insertion, repeating steps (c) through (g) using the modified treatment plan of an iteration of step (e) immediately preceding a current iteration of step (c), for the created treatment plan, said repeating until the evaluated total effect is substantially equivalent to that of the created treatment plan.

3. The method of claim 2 further comprising:
   positioning a needle template in proximity to the target tissue, the needle template having a plurality of working holes, each of the working holes having a location predefined in a template coordinate system;
   mapping the template coordinate system to the image coordinate system such that each of the working holes has a determinable location in the image coordinate system; and
   wherein the step of placing the needle includes inserting a needle through a working hole in the needle template as specified by the treatment plan.

4. The method of claim 3 further comprising the step of providing an obturator, wherein the needle template provides a guide aperture for removably holding the obturator and the target tissue is a prostate gland.

5. The method of claim 3 wherein the step of creating a treatment plan includes:
   determining a count of the number of needles to use;
   determining a position within the needle template for each needle;
   determining a depth of each needle insertion; and
   determining a count of the number of radiation seeds loaded into each needle.

6. The method of claim 3 wherein the steps of mapping, creating, acquiring, modifying and evaluating are performed using a digital processor, such that at least step (g) is performed using real-time imaging of the target tissue.

7. The method of claim 6 further comprising the step of evaluating final coverage using real-time imaging of the target tissue.

8. An image-guided method for implanting radiation seeds into target tissue comprising the steps of:
   (a) imaging the target tissue using an imaging system, the imaging system having a image coordinate system;
   (b) positioning a needle template in proximity to the target tissue, the needle template having a plurality of working holes, each of the working holes having a location predefined in a template coordinate system;
   (c) mapping the template coordinate system to the image coordinate system such that each of the working holes has a determinable location in the image coordinate system;
   (d) using images of the target tissue from the imaging system, creating a treatment plan for the target tissue;
   (e) in accordance with the created treatment plan, loading a needle with radiation seeds and placing the needle with respect to the target tissue;

(f) acquiring radiographic, geometric and dosimetric feedback on the placement of the needle with respect to the target tissue;

(g) modifying the created treatment plan based upon the acquired radiographic, geometric and dosimetric feedback, said modifying producing a modified treatment plan;

(h) placing the radiation seeds from the needle into the target tissue at a position relative to the needle and acceptable according to the modified treatment plan;

(i) evaluating total effect of placed radiation seeds;

(j) for each subsequent needle insertion, repeating steps (e) through (i) using the modified treatment plan of an iteration of step (g) immediately preceding a current iteration of step (e), for the created treatment plan, said repeating until the evaluated total effect is substantially equivalent to that of the created treatment plan;

wherein the step of placing the needle includes inserting a needle through a working hole in the needle template as specified by the treatment plan;

wherein
the imaging system is an interventional magnetic resonance imaging system;
the needle template is non-magnetic; and
the step of mapping includes calibrating the needle template using an array of light receivers mounted to the imaging system measuring at least three known calibration points on the needle template.

9. A real time dosimetry based implant and planning system comprising:
an imaging system having an image coordinate system;
a digital processor coupled to receive images from the imaging system; and
a treatment module executable by the digital processor, comprising:
a target definition submodule for selecting target tissue and sensitive areas based upon images generated by the imaging system;
a implant planning submodule for creating a treatment plan;
a validation submodule for providing in real-time radiographic, geometric and dosimetric feedback of needle placement with respect to the target tissue and sensitive areas during implantation.

10. The real time dosimetry based implant planning system of claim 9 further comprising:
a needle template containing working holes for the needles loaded with a determined amount of radiation seeds and calibration points for needle template registration, the needle template removably coupled to the imaging system and having a respective needle template coordinate system; and
in the treatment planning module,
a template registration submodule using the calibration points to define a mapping from needle template coordinates into imaging system coordinates.

11. The real time dosimetry based implant planning system of claim 10 wherein the needle template provides a guide aperture for removably holding an obturator; and
the target tissue is a prostate gland.

12. The real time dosimetry based implant planning system of claim 10 wherein the treatment plan comprises:
a count of the number of needles to use;
a position within the needle template for each needle;
a depth of each needle insertion; and
a count of the number of radiation seeds loaded into each needle.

13. The real time dosimetry based implant planning system of claim 9 wherein for each needle placed with respect to the target tissue, the treatment module updates the created treatment plan as a function of the radiographic, geometric and dosimetric feedback provided by the validation submodule, and the validation submodule utilizes real time images of the target tissue and sensitive areas generated from the imaging system.

14. The real time dosimetry based implant system of claim 9 wherein the validation submodule further provides an indication of final coverage using real-time images from the imaging system.

15. A real time dosimtery based implant and planning system comprising:
an imaging system having an image coordinate system;
a needle template containing working holes for the needles loaded with a determined a mount of radiation seeds and calibration points for needle template registration, the needle template removably coupled to the imaging system and having a respective needle template coordinate system;
a digital processor coupled to receive images from the imaging system; and
a treatment module executable by the digital processor, comprising:
a target definition submodule for selecting target tissue and sensitive areas based upon images generated by the imaging system;
a implant planning submodule for creating a treatment plan;
a validation submodule for providing in real-time radiographic, geometric and dosimetric feedback of needle placement with respect to the target tissue and sensitive areas; and
a template registration submodule using the calibration points to define a mapping from needle template coordinates into imaging system coordinates;
wherein:
the imaging system is an interventional magnetic resonance imaging system;
the needle template is non-magnetic; and
the template registration submodule utilizes an array of light receivers mounted to the imaging system measuring at least three known calibration points on the needle template.

* * * * *